United States Patent [19]
Lai

[11] Patent Number: 5,489,711
[45] Date of Patent: Feb. 6, 1996

[54] SYNTHETIC LUBRICANT ANTIOXIDANT FROM MONOSUBSTITUTED DIPHENYLAMINES

[75] Inventor: John T. Lai, Broadview Heights, Ohio

[73] Assignee: The B. F. Goodrich Company

[21] Appl. No.: 359,679

[22] Filed: Dec. 20, 1994

[51] Int. Cl.$^6$ .................................................. C07C 211/55
[52] U.S. Cl. ............................ 564/434; 252/50; 524/255; 564/309; 564/310; 564/311; 564/314; 564/408; 564/433
[58] Field of Search .................................. 564/309, 310, 564/311, 314, 408, 433, 434; 524/255; 252/50

[56] References Cited

U.S. PATENT DOCUMENTS

| | | | |
|---|---|---|---|
| 3,206,405 | 9/1965 | Hepplewhite et al. | 252/56 |
| 3,247,111 | 4/1966 | Oberright et al. | 252/34.7 |
| 3,492,233 | 1/1970 | Hepplewhite et al. | 252/51.5 |
| 3,509,214 | 4/1970 | Braid et al. | 260/576 |
| 3,573,206 | 3/1971 | Braid et al. | 252/51.5 |
| 3,655,559 | 4/1972 | Holt | 252/51.5 A |
| 3,660,290 | 5/1972 | Schlobohm | 252/51.5 A |
| 3,759,996 | 9/1973 | Braid | 260/570 |
| 3,773,665 | 11/1973 | Braid | 252/50 |
| 3,804,762 | 4/1974 | Jervis et al. | 252/50 |
| 5,321,159 | 6/1994 | Lai et al. | 564/437 |

Primary Examiner—Richard L. Raymond
Attorney, Agent, or Firm—Mary Ann Tucker; Samuel B. Laferty

[57] ABSTRACT

An oligomer from diarylamines is disclosed which has desirable antioxidant properties in lubricating oils which contain synthetic ester lubricants. The oligomer is desirable for use at higher temperatures where it has less volatility than simple diarylamines. The oligomer has substantial portions of monosubstituted diphenylamine repeat units which result in linear oligomers. Di and polysubstituted diphenylamines may optionally be present as repeat units. These di and polysubstituted diphenylamines generally react as monofunctional reactants in oligomerization and tend to reduce the number of repeat units in the average oligomer.

15 Claims, No Drawings

SYNTHETIC LUBRICANT ANTIOXIDANT FROM MONOSUBSTITUTED DIPHENYLAMINES

FIELD OF THE INVENTION

The present invention relates to an oligomeric antioxidant desirable for use in synthetic oil lubricants. The oligomeric antioxidant is the reaction product of chemically coupling one or more monosubstituted diphenylamines with themselves and optionally with other diaromatic amines.

BACKGROUND OF THE INVENTION

Amine antioxidants have been known and are widely used to improve the thermal-oxidative stability of synthetic ester lubricants used in the lubrication of moving parts operated at very high temperature, such as jet engines and hydraulic systems for military and commercial aircraft. In operation at high temperature in the presence of oxygen and catalytically active metals, the antioxidants are depleted. Oxidative oil degradation can create acidic by-products that degrade nearby metals and can form polymers which undesirably increase the viscosity of the lubricant. This oxidative degradation can also lead to undesirable oil insoluble sludge and deposits.

U.S. Pat. No. 3,655,559 discloses alkylated diphenylamines.

Disubstituted diphenylamines are preferred as antioxidants over monosubstituted diphenylamines because of their enhanced activity as antioxidants. Disubstituted diphenylamines are commercially available. Monosubstituted diphenylamines are not known to be commercially available in pure form because of their reduced activity. Vanlube® 848 from R. T. Vanderbilt having from about 20 to about 30 mole % of monosubstituted diphenylamines in monomer form along with a variety of other diphenylamines (nonsubstituted, disubstituted, etc.) became commercially available only as recently as 1987. Oligomeric antioxidants tend to have better performance at higher temperatures than their monomeric precursors.

It is the object of this disclosure to prepare one or more oligomeric antioxidants from at least monosubstituted diphenylamine which may be used in lubricating oils to provide better oxidation resistance.

SUMMARY OF THE INVENTION

Monosubstituted diphenylamines were found to readily oligomerize under a variety of conditions to produce higher molecular weight molecular weight oligomers with enhanced performance in thermal oxidation tests. Disubstituted and polysubstituted diphenylamines could not be oligomerized to a large extent to form oligomers higher than dimers. Blends of monosubstituted diphenylamines with di or polysubstituted diphenylamines were also found to easily oligomerize to useful antioxidants.

DETAILED DESCRIPTION OF THE INVENTION

Diphenylamines without substituents are readily oligomerized, but will eventually crosslink into insoluble material. Disubstituted diphenylamines are more effective antioxidants than diphenylamines having only hydrogen substituents. Disubstituted and polysubstituted diphenylamines, although very active as antioxidants, are not easily homooligomerized and usually in oligomerization reactions only dimers can be formed from disubstituted diphenylamines having one or more nonhydrogen substituent present on each aromatic ring.

Monosubstituted diphenylamines which are not generally commercially available were found to easily oligomerize forming generally linear oligomers with number average degrees of polymerization from about 2 to about 50 and desirably from about 2 to about 10. These are desirable antioxidants. Monosubstituted diphenylamines also can be oligomerized with di and polysubstituted diphenylamines having one or more nonhydrogen substituent on each aromatic ring. The cross-oligomers of mono substituted diphenylamines with di or polysubstituted diphenylamines are desirable as antioxidants. In reactions forming oligomers from diphenylamines, it is easy to control the degree of polymerization by the relative amounts of monosubstituted diphenylamine to di and polysubstituted diphenylamine having one or more nonhydrogen substituent per ring. Nonsubstituted diphenylamines may be included in small amounts such as less than 20 or less than 10 mole percent of the total diphenylamines. It is desirable that N-aryl naphthylamines in non, mono, di, or polysubstituted form (wherein the substituents can be the same as $R^1$) be present in amounts less than 25 mole percent based on the total of N-aryl naphthylamines and diphenylamines, more desirably having less than 10 mole percent or no N-aryl naphthylamines present at all.

In that the monosubstituted diphenylamine readily oligomerizes, it is considered to be a difunctional reactant in oligomerization reactions. The di and polysubstituted diphenylamines having one or more nonhydrogen substituent on each aromatic ring are considered monofunctional reactants in oligomerization reactions. The diphenylamines having only hydrogen substituents are considered trifunctional or polyfunctional (3 or more) in oligomerization reactions of diphenylamines. Diarylamines will be used to describe diphenylamines with any number of substituent group and to describe other diarylamines such as N-aryl naphthylamine.

The preferred monosubstituted diphenylamine has the following structure:

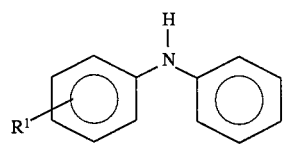

where $R^1$ can be a linear or branched alkyl, alkenyl, or aralkyl having from about 1 to about 20 carbon atoms, more desirably from about 4 to about 16. The aralkyl substituents can be created by reacting, e.g., styrene, alphamethylstyrene, or paramethylstyrene, with diphenylamines. $R^1$ is preferably a tertiary alkyl group, e.g., t-octyl. One skilled in the art will appreciate that the designation of the $R^1$ groups entering the side of a ring structure indicate the $R^1$ groups may be ortho, meta, or para to the nitrogen. Desirably the monosubstituted diphenylamines form from about 10, 15, or 20 to about 100 mole percent of the repeat units of the oligomeric antioxidants, more desirably from about 20, 25 or 40 to about 90 percent, and most desirably from about 60 to about 75 mole percent. Desirably these oligomers are produced from diarylamine solutions wherein said one or more monosubstituted diphenylamines are from about 10, 15 or 20 mole percent to about 100 mole percent, more desirably from about 20, 25 or 40 mole percent to about 90 mole percent and preferably from about 60 to about 75 mole percent of the total diarylamines of said solution.

The preferred di or polysubstituted diphenylamines have the following structure:

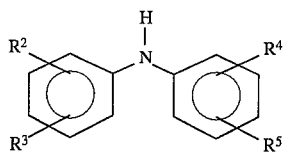

where each $R^2$, $R^3$, $R^4$, and $R^5$ is independently a hydrogen or the groups of $R^1$ as described above, provided that at least one of $R^2$ and $R^3$ must be other than hydrogen and one of $R^4$ and $R^5$ must be other than hydrogen. Desirably from about 5 to about 80, 85 or 90 percent of the repeat units of the oligomeric antioxidant are the di or polysubstituted diphenylamine, more desirably from about 10 to about 60, 75 or 80 mole percent and preferably from about 25 to about 40 mole percent. Desirably the di or polysubstituted diphenylamine is disubstituted diphenylamine. Desirably these oligomers are produced from diarylamine solutions wherein said one or more di or polysubstituted diphenylamines are present in amounts from about 5 to about 80, 85 or 90 mole percent, of the total diarylamines more desirably from about 10 to about 60, 75, or 80 mole percent and preferably from 25 to 40 mole percent.

Other diarylamines may be present in the oligomeric antioxidant and in the diarylamine solutions used to form the oligomers in the residual amounts to those recited. These diarylamines include nonsubstituted diphenylamines, and phenothiazines with zero, one or two substituents.

It is theorized that the bonding between the one or more monosubstituted diphenylamine (DPA) and optionally disubstituted or polysubstituted diphenylamine (DPA) or optionally other diarylamines may occur between two nitrogen atoms, between a nitrogen atom in one diarylamine and a carbon atom in another diarylamine or between carbon atoms in two different aryl rings. The possible linkages of aromatic diamines are described in detail in U.S. Pat. No. 3,509,214, which is herein incorporated by reference.

The antioxidant of the present invention is made by reacting one or more monosubstituted diphenylamines (DPA) with themselves or optionally with one or more other diarylamines to form oligomeric products which are effective antioxidants at elevated temperatures. The reaction can be generalized as follows.

Preferably the oligomeric antioxidant is formed by the reaction of a monosubstituted diphenylamine with itself or with one or more di or polysubstituted diphenylamine having one or more nonhydrogen substituent group per ring thereof), and optionally with other diarylamines at temperatures from about 40° C. to about 200° C., more desirably from about 70° to about 200° C., preferably from about 90° or 110° to about 180° C. and most preferably from about 130° to about 150° C. for from about 30 minutes to about 30 hours, desirably from about 1 to about 10 hours, and preferably from about 2 to about 6 hours. Any solvent may be used but preferably the solvent is a synthetic ester lubricant or one or more alkanes. Preferably an organic peroxide is present at these temperatures to cause oligomerization. A supply of $N_2$ or other gas inert to peroxides and radicals therefrom is desirably used to purge air from the reactor.

Alternatively, the reaction may be conducted in bulk or solution by simply heating the one or more monosubstituted diphenylamines optionally with one or more other arylamines at a temperature desirably in the range of from about 150° to about 300° C. and preferably from about 200° to about 275° C. The one or more diphenylamines may be dissolved in a suitable inert or organic solvent such as an aromatic hydrocarbon ketone and the like. A stream of gas such as air, oxygen, or $N_2$ or another inert gas can be circulated through the liquid mixture during the heating step. The heating step may occur from about 30 minutes to about 80 hours.

Alternatively the oxidation and coupling of the one or more diphenylamines may be performed using a chemical reagent. Useful chemical reagents include potassium permanganate and alkyl or aryl peroxides. These oxidations may be performed at any suitable temperature using known techniques. As above, various gases can be added during the reaction to provide oxygen or an inert environment. The residue from the oxidizing agent is removed if necessary. Filtration may be used to remove solid residue, and the filtrate may be stripped of solvent if desired as the final purification step.

The simple alkyl peroxides like butyl peroxide are preferred because their decomposition products can be easily removed as aliphatic alcohols at reasonably low temperatures. The individual components (reactants) may be added in any order, in increments, or metered into other components. The reaction may be carried out under vacuum to remove volatiles from the decomposition of the organic peroxides. The reaction can also be carried out under pressure to keep the volatiles in. Solvents such as aliphatic hydrocarbons and synthetic ester lubricants having abstractable hydrogens can be used with the organic peroxide oligomerization method.

The synthetic ester lubricants are produced from condensation of one or more monohydroxy alcohols and/or one more polyhydroxy alcohols with at least one monocarboxylic and/or at least one polycarboxylic acids. These ester fluid lubricants are described in detail later in this specification.

These ester lubricants are disclosed in U.S. Pat. No. 3,492,233 which is hereby incorporated by reference, and can become chemically bonded through dehydrocondensation reactions to the one or more diphenylamines (DPA) or oligomers thereof during the oligomerization reaction of the DPA. However, with careful control of the amount of peroxide used and the reaction temperature, the amount of dehydrocondensation bonding between the ester lubricant and diphenylamine or other diarylamine is minimized. Desirably less than 30, more desirably less than 20, and preferably less than 10 mole of the total diarylamines chemically are condensed with the ester lubricants or alkane solvents.

Another useful solvent for the reaction is the alkane solvents having from about 6 to about 16 carbon atoms having linear, branched, or cyclic structure. These are also known to form dehydrocondensation products with diphenylamines, but this dehydrocondensation reaction with solvents is limited in the organic peroxide method by the reaction conditions. The alkane solvents are easily removed by volatilization.

Subsequent to the reaction of the organic peroxides, it is desirable to raise the temperature to fully decompose the residual organic peroxides. This minimizes undesirable oxidation reactions later. Under optimized conditions as disclosed herein, most of the desired reactions which form oligomers and cross oligomers have occurred prior to the residual peroxide decomposition step. Desirably, this peroxide decomposition is conducted at temperatures from about 140° to about 200° C., and desirably from about 160° to about 180° C. for from about 5 minutes to about 2 hours, more desirably from about 30 minutes to about 1 hour, and desirably at pressures below atmospheric pressure. Desirably, at least 70 mole percent of the diphenylamine and other diarylamine reactants are converted into oligomeric form with less than 30 mole percent remaining in monomer form. Oligomers or oligomeric form for the purpose of this application will desirably include dimers, trimers, etc. up through a number average degree of polymerization of 10 or 50.

Any organic peroxide may be used as a free radical source which has a half-life of about one hour at a temperature between from about 70° C. to about 200° C. Desirably, the half-life of one hour is at a temperature between from 90° to about 160° C., and preferably between from about 130° to about 150° C. Included in this group are the acyl peroxides, peresters, peroxyketals, and alkyl peroxides, all of which are commercially available from Lucidol Penwalt, U.S.A. Atochem or Akzo Chemicals, Inc., by the trademarks or common names indicated. The amount of peroxide used is desirably from about 0.5 to about 2.5 mole/mole of the diphenylamines and other diarylamines and is preferably from about 0.6 to about 1.5, and most preferred from about 0.8 to about 1.3 mole/mole of diphenylamines and other diarylamines.

Included as peroxides are acyl peroxides of the formula

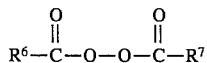

peroxyketals of the formula $(R^6)_2C(OOR^7)_2$, alkyl peroxides of the formula $R^6$-O-O-$R^7$, and peresters of the formula

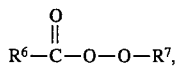

wherein $R^6$ and $R^7$ can be the same or different and may be an alkyl, aromatic, alkyl substituted aromatic, or aromatic substituted alkyl groups having from 1 to about 10 carbon atoms.

Suitable peresters include t-amylperoxy-2-ethylhexanoate, t-butylperoxy-2-ethylhexanoate (t-butyl peroctoate), t-butylperoxy-isobutylrate, t-butylperoxy-maleic acid, OO-t-butyl O-isopropyl monoperoxycarbonate, 2,5-dimethyl-2,5-di(benzoylperoxy) hexane, OO-t-butyl-O-(2-ethyl-hexyl)mono peroxycarbonate, OO-t-amyl O-(2-ethylhexyl)mono peroxy-carbonate, t-butyl-peroxy acetate, t-amyl-peroxy-acetate, t-butylperoxy benzoate, t-amylperoxybenzoate and di-t-butyl-diperoxyphthalate.

Suitable peroxyketals include n-butyl-4,4-bis(tbutylperoxy)valerate, 2,2-di(t-butylperoxy) butane, ethyl-3,3-di(t-butylperoxy)butyrate, 2,2-di(t-amylperoxy)propane and ethyl-3,-3-di(t-amylperoxy) butyrate.

Suitable dialkyl peroxides include dicumyl peroxide, 2,5-dimethyl-2,5-di(t-butylperoxy) hexane, t-butyl cumyl peroxide α-bis(t-butylperoxy) diisopropylbenzene, di-t-butyl peroxide, di-t-amyl peroxide and 2,5-dimethyl-2,5 -di(t-butylperoxy) hexane-3. The preferred peroxide is di-t-butyl peroxide.

The antioxidants of this invention are useful in ester fluids including lubricating oils, fuels, hydraulic fluids, transmission fluids, compressor lubricant (such as compressors used in refrigeration units), and especially those synthetic ester fluids useful in high temperature avionic (turbine engine oils) applications and/or internal combustion reciprocating or rotary engine oils. The antioxidants are also useful in blended oils for similar purposes that desirably have at least 10, 20, or 30 or more desirably at least 50 weight percent synthetic ester fluids with the remainder being predominantly other lubricants such as hydrocarbon oils or poly-α-olefin oils.

The synthetic ester fluid lubricants which may be used with this invention are esters produced from monohydroxy alcohols and monocarboxylic acids, from polyhydroxy alcohols and monocarboxylic acids, and/or from monohydroxy alcohols and dicarboxylic acids. Such esters are well known, having been described for example in U.S. Pat. No. 3,432,433 which is incorporated herein by reference. Each of the alcohols and acids used in preparing the ester may contain from about 1 to about 4 functional groups thereby producing mono-, di-, tri-, and tetraesters. Contemplated within this invention are esters of alcohols, diols, triols, and pentaerythritols, said alcohols or polyols having from about 2 to about 20 carbon atoms, and mono- and dicarboxylic acids having from about 2 to about 20 carbon atoms and preferably from about 4 to about 12.

The above esters may include the monoesters from octyl acetate, decyl acetate, octadecyl acetate, methyl myristate, butyl stearate, methyl oleate, and the like and the polyesters from dibutyl phthalate, di-octyl adipate, di-2-ethylhexyl azelate, di-2-ethylhexyl sebacate, and the like.

The most preferred esters are produced from hindered or neopentyl alcohols and pentaerythritol, that is, those in which the beta carbon atom is completely substituted by other carbon atoms. These esters have the structure

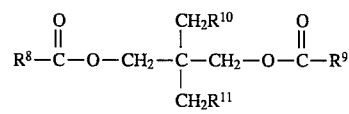

wherein each of $R^8$ and $R^9$ is individually an alkyl or aryl of about 1 to about 19 carbon atoms and each of $R^{10}$ and $R^{11}$ is individually hydrogen, alkyl of about 1 to about 5 carbon atoms or

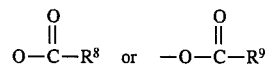

and each of the $R^8$ and $R^9$ groups are as described above. Such esters include 2,2-dimethylpropane-1,3-diol dipelargonate, trimethylolpropane trioctanoate, trimethylolpropane tridecanoate, trimethylolbutane trihexanoate, pentaerythritol tetraoctanoate and pentaerythritol tetradodecanoate. Mixtures of acids may be used in producing the di-, tri- and tetraesters. For example, a preferred pentaerythritol ester contains a mixture of $C_4$ through $C_{10}$ carboxylic acids. The esters in accordance with this invention include any ester fluid having an abstractable hydrogen atom, although the preferred reaction conditions result in minimal dehydrocondensation between the polyesters and the amines.

The oligomeric antioxidant stabilizer made from one or more monosubstituted diphenylamines and optionally other diarylamines is efficient at concentrations from about 0.1 to about 20 weight percent, desirably from about 0.5 to about 10 weight percent, more desirably from about 0.5 to about 5 wt. % percent and preferably from about 1.5 to about 2.0 weight percent in a lubricant based upon the total weight of the formulated lubricant. These weight percents are of the diphenylamines and other diarylamines in the oligomers and do not include the synthetic ester lubricants even if they are used as a solvent for the reaction. In the case of synthetic ester lubricants coreacted with one or more diphenylamines forming co-condensation products, the weight percents recited above are the calculated weight percents of said one or more diphenylamine and optional diarylamine reactants in the final lubricant product. The stabilizer can be used in conjunction with other additives such as detergents, dispersants, other antioxidants, corrosion inhibitors, antifoamants, antiwear additives, extreme pressure additives, hydrolytic stability agents, load additives or viscosity modifiers. One such antioxidant can be the DPA monomer or other oligomeric products having DPA repeat units.

The effectiveness of the oligomeric antioxidant composition in synthetic ester oils is enhanced by adding a triazine, for example an alkylamino symmetrical triazine such as hexabutyl melamine or a coupled triazine such as $N^1,N^4$-piperazine-bis-(2-[4,6-bis-dibutylamine-1,3,5-triazine]). These triazines are prepared by methods known in the art. U.S. Pat. No. 3,322,763 discloses how to prepare coupled triazines and is incorporated herein by reference. The amount of triazine is desirably from about 0.01 to about 5 grams per 100 grams of lubricant.

The following non-limiting examples will provide the reader with a more detailed understanding of the invention.

General procedure for making coupled diarylamine oligomers

Diarylamine A (X mole), diarylamine B (Y mole) were mixed with an ester lubricant or a hydrocarbon solvent under inert atmosphere. The weight of ester lubricant or hydrocarbon solvent was the same as the total weight of diarylamines starting materials. The mixture was heated at 140° to 145° C. and a t-butyl peroxide [in amount of 1.3 (X+Y) mole] was added dropwise over a 30 min. to a one hour period. The t-butyl alcohol formed from the decomposition of t-butyl peroxide was distilled off while maintaining the temperature at 140° to 145° C. for 1 to 5 hours. The temperature was raised to a temperature of 170° to 175° C. to remove most of the t-butyl alcohol and any hydrocarbon solvent. The resulting mixture was either a 50 percent product in ester lubricant, a 100 percent neat product, or a powdered solid after being ground.

The oligomers and blends in the following Table I are identified below. Oligomer 184 is the oligomerization product from V-848 which is a physical blend of ~0–5% diphenylamine, ~35–45% p,p'-di(t-butyl and/or t-octyl) diphenylamine, ~20–30% p(t-butyl or t-octyl) diphenylamine, ~5–15% p-(t-butyl-p'-t-octyldiphenylamine) and 5–40% unidentified alkylated diphenylamines with V-81 which is p,p'-di-t-octyldiphenylamine in the mole ratio of V-848 to V-81 diarylamines of 2 to 1. Oligomer 186 is the oligomerization product of V-81 (already described) and MOD which is p-t-octyldiphenylamine in the mole ratio of diarylamines from the two starting materials of 2 to 1. Oligomer 188 is the oligomerization product of the same two diamines as was oligomer 186 but the oligomerization reaction was conducted in an ester lubricant. Oligomer 185 has the same starting diamines as oligomer 184 but was oligomerized in the presence of a synthetic ester lubricant. Oligomer 190 is an oligomerization product of V-848 (already described) with itself. Oligomer 197 is a homooligomer of MOD which is p-t-ocytldiphenylamine. Oligomer 198 is an oligomerization product of V-81 (an already described disubstituted diphenylamine) and MOD is a monosubstituted diphenylamine reacted in a mole ratio of monosubstituted to disubstituted of 2 to 1. Control 1 is an oligomerization product of a disubstituted diphenylamine with an N-aryl naphthylamine. Control 2 is a physical blend of disubstituted diphenylamine with an N-aryl naphthylamine. Irganox® from Ciba Geigy (LO-6) is N-p-t-octylphenyl-1-naphthylamine.

The following Table I shows the performance of the above recited oligomers of diphenylamines in a standardized oxidation stability test Federal Test Method Standard No. 791B,5308.6 at 400° F. (204° C.) for 72 hours. The tested samples contain the specified weight percent of the oligomeric diamine reaction product, 2 wt. % triaryl phosphate, and 0.1 wt. % tolyltriazole in a synthetic ester lubricant made from a mixture of $C_5$ to $C_{10}$ carboxylic acids and pentaerythritol. Oxidation stability was measured by the percentage change in viscosity (centistokes at 40° C.) (Δ Vis) and change in total acid number (Δ TAN). The Δ TAN is calculated from the moles of additional base required to titrate or neutralize 100 g of sample multiplied by 561.

TABLE I

| | Oligomer | Δ Vis (%) | Δ TAN | Comments |
|---|---|---|---|---|
| 1 | 184 (2%) | 37.4 | 7.5 | 184 is a coupled diarylamine (V-848)$_2$ (V-81)$_1$ (solid) |
| 2 | 186 (2%) | 38.2 | 7.65 | 186 is a coupled diarylamine of (V-81)$_2$ (MOD)$_1$ (solid) |
| 3 | 188 (4%) | 46.3 | 6.3 | 188 is a coupled diarylamine of (V-81)$_2$ (MOD)$_1$ (50% in ester) |
| 4 | 185 (4%) | 39.0 | 8.29 | 185 is a coupled diarylamine of (V-848)$_2$ (V-81)$_1$ 50% in ester |
| 5 | 190 (4%) | 31.8 | 7.6 | 190 is simply (V-848)$_n$ 50% in ester |
| 6 | 197 (4%) | 30.5 | 5.4 | 197 is a homooligomer of MOD 50% in ester |
| 7 | 198 (4%) | 33.6 | 6.9 | 198 is a coupled diarylamine of (V-81)$_1$ (MOD)$_2$, 50% in ester |
| 8 | Control 1 (4%) | 46.2 | 11.5 | Control 1 is coupled oligomer (V-81)$_2$ (LO-6)$_1$ prepared 50% in ester |
| 9 | Control 2 (2%) | 58 | 13 | Control 2 is a combination of V-81 and LO-6 in a 1 to 1 wt. ratio |

Oligomers 184 and 185 contains mixtures of monosubstituted and disubstituted diphenylamines in a mole ratio of 0.25 to 1.

Oligomer 186 and 188 contain mixtures of monosubstituted and disubstituted diphenylamines in a mole ratio of 1 to 2.

Oligomer 190 contains mixtures of monosubstituted and disubstituted diphenylamines in a mole ratio of 1 to 2.

Oligomer 197 contains monosubstituted diphenylamines only.

Oligomer 198 contains mixtures of monosubstituted and disubstituted diphenylamines in a mole ratio of 2 to 1.

The control 1 oligomer contains mixtures of disubstituted diphenylamines and 1-phenylnaphthylamine in a mole ratio of 2 to 1.

The control 2 is a blend of disubstituted diphenylamine and a substituted phenylnaphthylamine.

While in accordance with the patent statutes the best mode and preferred embodiment have been set forth, the scope of the invention is not limited thereto, but rather by the scope of the attached claims.

What is claimed is:

1. An oligomeric reaction product comprising repeat units from a monosubstituted diphenylamine, wherein said monosubstituted diphenylamine before coupling is one or more monosubstituted diphenylamines having the formula

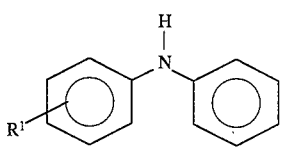

where $R^1$ is independently an alkyl, alkenyl, or aralkyl group having from 1 to 20 carbon atoms, wherein said oligomeric reaction product has from about 10 to 100 mole percent of the repeat units from said one or more monosubstituted diphenylamines.

2. An oligomeric reaction product according to claim 1, further comprising repeat units from one or more di or polysubstituted diphenylamines having one or more nonhydrogen substituent on each phenyl ring, said di or polysubstituted diphenylamine before coupling being of the formula

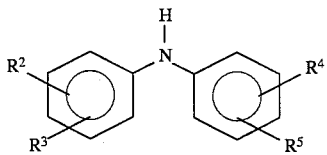

said $R^2$ through $R^5$ independently of each other and independently on subsequent repeat units being a hydrogen, a linear or branched alkyl, alkenyl, or aralkyl group having 1 to 20 carbon atoms, wherein said di or polysubstituted diphenylamines are from about 5 to about 90 mole percent of the repeat units of said oligomeric product.

3. An oligomeric product according to claim 1, having a number average degree of polymerization of from about 2 to about 10.

4. An oligomeric product according to claim 2, having a number average degree of polymerization from about 2 to about 10.

5. An oligomeric product according to claim 4, wherein said di or polysubstituted diphenylamines are from about 10 to 80 mole percent and said monosubstituted diphenylamines are from about 20 to about 90 mole percent of the repeat units of said oligomeric product.

6. An oligomeric product according to claim 2, wherein said di or polysubstituted diphenylamines are from about 10 to about 80 mole percent and said monosubstituted diphenylamines are from about 20 to about 90 mole percent of the repeat units of said oligomeric product.

7. An oligomeric product according to claim 1, wherein said one or more monosubstituted diphenylamines are from 60 to 75 mole percent of the repeat units of said oligomeric product.

8. An oligomeric product according to claim 7, wherein said di or polysubstituted diphenylamines are from about 25 to 40 mole percent of the repeat units of said oligomers, and wherein said $R^1$ on said monosubstituted diphenylamines and said $R^2$, $R^3$, $R^4$ and $R^5$ groups of said polysubstituted diphenylamines when present comprise tertiary alkyl groups or aralkyl groups.

9. An oligomeric product according to claim 1, present from about 0.1 to about 20 weight percent in a lubricating oil which lubricating oil comprises at least 20 wt. % synthetic ester oil based on the total lubricant weight.

10. A process for making an antioxidant, comprising;

reacting a diarylamine solution comprising from about 10 to about 100 mole percent of one or more monosubstituted diphenylamines based on the total diarylamines of said solution;

said one or more monosubstituted diphenylamines having the formula

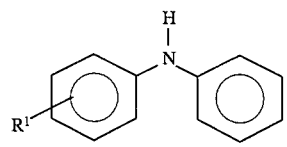

where $R^1$ is an alkyl, alkenyl, or aralkyl group having from about 1 to about 20 carbon atoms;

in a dehydrocondensation reaction to form one or more oligomers.

11. A process according to claim 10, wherein said diarylamine solution further comprises one or more di or polysubstituted diphenylamines having one or more nonhydrogen substituent on each phenyl ring, wherein said one or more di or polysubstituted diphenylamines have the formula

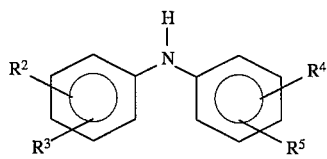

said $R^2$ through $R^5$ independently of each other and independently on subsequent repeat units being a hydrogen, a linear or branched alkyl, alkenyl, or aralkyl group having 1 to 20 carbon atoms, wherein said di or polysubstituted diphenylamines are from about 5 to about 90 mole percent said diarylamines of said diarylamine solution.

12. A process according to claim 11, wherein said one or more monosubstituted diphenylamines and said one or more di or polysubstituted diphenylamines are reacted at a temperatures from about 70° to about 200° C. in the presence of a peroxide to form said one or more oligomers.

13. A process according to claim 11, wherein said one or more oligomers have a number average degree of polymerization from about 2 to about 10.

14. A process according to claim 13, wherein said one or more monosubstituted diphenylamines are present from about 20 to about 90 mole percent and said one or more di or polysubstituted diphenylamines are present from about 10 to about 80 mole percent in said diarylamine solution.

15. A process according to claim 10, wherein said diarylamine solution is reacted at a temperature from about 70° to about 200° C. in the presence of a peroxide to form said oligomers, and wherein said $R^1$, $R^2$, $R^3$, $R^4$, and $R^5$ groups, when present, comprise tertiary alkyl groups or aralkyl groups.

* * * * *